(12) United States Patent
Shih et al.

(10) Patent No.: US 8,969,410 B1
(45) Date of Patent: Mar. 3, 2015

(54) PHARMACEUTICAL COMPOSITION FOR ALLEVIATING OR TREATING GOUT AND USES THEREOF

(71) Applicant: Industrial Technology Research Institute, Hsinchu (TW)

(72) Inventors: Ying-Chu Shih, Hsinchu County (TW); Jenn-Line Sheu, Hsinchu (TW); Cheng-Yu Lee, Hsinchu (TW); Jir-Mehng Lo, Hsinchu County (TW); Yi-Ching Lee, Hsinchu (TW); Ying-Fei Tsai, Hsinchu (TW); Yi-Cheng Cheng, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 14/497,343

(22) Filed: Sep. 26, 2014

(30) Foreign Application Priority Data

Dec. 24, 2013 (TW) .............................. 102148017 A (51) Int. Cl.
*A61K 31/365* (2006.01)
*C07D 307/77* (2006.01)
*A61K 31/222* (2006.01)
*A61K 36/9062* (2006.01)
*A61K 36/53* (2006.01)

(52) U.S. Cl.
CPC ............ *A61K 31/365* (2013.01); *A61K 31/222* (2013.01); *A61K 36/9062* (2013.01); *A61K 36/53* (2013.01)
USPC ............ 514/468; 549/263; 549/299; 514/461

(58) Field of Classification Search
CPC ........................... A61K 31/365; C07D 307/77
USPC ......................... 549/263, 299; 514/461, 468
See application file for complete search history.

(56) References Cited

U.S. PATENT DOCUMENTS

| 6,420,561 B1 | 7/2002 | Haruta et al. |
| 6,566,405 B2 | 5/2003 | Weidner et al. |
| 2003/0157204 A1 | 8/2003 | Weidner et al. |
| 2011/0262567 A1 | 10/2011 | Kang et al. |

FOREIGN PATENT DOCUMENTS

| TW | 410218 | 11/2000 |
| TW | 201225970 | 7/2012 |

OTHER PUBLICATIONS

Grzanna et al., "Ginger Extract Inhibits beta-Amyloid Peptide-Induced Cytokine and Chemokine Expression in Cultured THP-1 Monocytes," The Journal of Alternative and Complementary Medicine, Dec. 2004, pp. 1009-1013.
Daubresse et al., "A Mild Synthesis of Coumaryl, Coniferyl, Sinapyl Aldehydes and Alcohols," Synthesis, Apr. 1994, pp. 369-371.
Ryckman et al., "Role of S100A8 and S100A9 in Neutrophil Recruitment in Response to Monosodium Urate Monohydrate Crystals in the Air-Pouch Model of Acute Gouty Arthritis," Arthritis & Rheumatism, Aug. 2003, pp. 2310-2320.
Tadataka Noro et al. "Inhibitors of Xanthine Oxidase from Alpinia galanga", 1988, p. 244-248, Chemical & pharmaceutical bulletin 36.1.

*Primary Examiner* — Golam M M Shameem
(74) *Attorney, Agent, or Firm* — Jianq Chyun IP Office (57) ABSTRACT

A pharmaceutical composition for alleviating or treating gout and the applications thereof are provided. The pharmaceutical composition includes p-coumaryl diacetate as an active ingredient.

14 Claims, 5 Drawing Sheets

PHARMACEUTICAL COMPOSITION FOR ALLEVIATING OR TREATING GOUT AND USES THEREOF

CROSS-REFERENCE TO RELATED APPLICATION

This application claims the priority benefit of Taiwan application serial no. 102148017, filed on Dec. 24, 2013. The entirety of the above-mentioned patent application is hereby incorporated by reference herein and made a part of this specification.

BACKGROUND

1. Technical Field

The technical field relates to a pharmaceutical composition for alleviating or treating gout and the applications thereof.

2. Description of Related Art

Gout is one of the common metabolic diseases and the conditions of gout are usually characterized by deposition of uric acid crystals and inflammatory arthritis at the toes, ankles, knees, wrists, fingers, elbows and other joints. In particular, when the uric acid concentration in the blood exceeds the threshold metabolizable by the kidney, the excessive urate will form crystals (so called trophi) accumulated in the joints, which will cause acute inflammatory arthritis and inflammation of the joints or tissues around the joints. Currently, the treatment of gout may generally be categorized as nonsteroidal anti-inflammatory drugs (NSAIDs), corticosteroids, colchicine and uric acid lowering drugs. The treatment of the acute onset of gout usually adopts nonsteroidal anti-inflammatory drugs (NSAIDs), corticosteroids or colchicine. However, the majority of these drugs have considerable side effects. Hence, it is desirable to develop the treatment of gout with less side effects and better efficacy.

SUMMARY

The present disclosure provides a pharmaceutical composition as a medicament for alleviating or treating gout. The pharmaceutical composition comprises p-coumaryl diacetate as an active ingredient.

The present disclosure provides a pharmaceutical composition for alleviating or treating gout, comprising p-coumaryl diacetate and ovatodiolide, and the weight ratio of p-coumaryl diacetate to ovatodiolide ranges from 10:90 to 85:15.

The disclosure further provides a method for alleviating or treating gout by administrating a medicament comprising a pharmaceutical composition that comprises p-coumaryl diacetate as an active ingredient and optionally ovatodiolide.

To make the aforementioned and other features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

The following examples and experimental examples are provided to further illustrate various embodiments of the invention.

In addition, in the present disclosure, chemical structures of the compounds are sometimes represented using the skeleton formula. This type of representation may omit carbon, hydrogen and carbon-hydrogen bond. Certainly, for structural formulas drawn with clear functional groups, the illustration prevails.

In one embodiment, the present disclosure provides a pharmaceutical composition for alleviating or treating gout. The pharmaceutical composition comprises at least p-coumaryl diacetate (CDA) as one active ingredient.

Paracoumaryl diacetate (p-coumaryl diacetate) has a molecular formula as $C_{13}H_{14}O_4$, named as 4-(3-acetoxy-propenyl)-phenyl acetate and has the following chemical formula (1):

(1)

and the cis/trans isomers of the chemical formula (1) are included herein.

P-coumaryl diacetate may be chemically synthesized as referenced to the article "A Mild Synthesis of Coumaryl, Coniferyl, Sinapyl Aldehydes and Alcohols", *Synthesis-stuttgart* January 1994; 1994(04):369-371, DOI:10.1055/s-1994-25477 by Nicolas Daubresse, Charlette Francesch, Farida Mhamdi and Christian Rolando, and the details will not be repeated herein again.

Of course, p-coumaryl diacetate may be extracted from the plants, such as the plant *Alpinia galanga*.

According to one embodiment of the present disclosure, the plant *Alpinia galanga* is used for extraction by extracting the root of the plant *Alpinia galanga* with the organic solvent(s). The solvent used may be one or more types of straight-chain or branched-chain saturated alkanes with 4-10 carbon atoms (C4-C10), used singly or as a mixture thereof. Alternatively, the solvent for extraction may be one or more types of straight-chain or branched-chain unsaturated alkenes or alkynes with 4-10 carbon atoms (C4-C10), used singly or as a mixture thereof. The solvent used for extraction may be the mixture of C4-C10 alkanes, alkenes and alkynes. In one embodiment of the present disclosure, the extraction solvent is heptane of a concentration of 95% or 100% (v/v), for example.

The extraction temperature and time may be determined based on the nature of the solvent and other reaction conditions, and there are no particular limitations. In one embodiment of the present disclosure, the extraction temperature may be the room temperature, and the extraction time may be about 72 hours.

The extraction method used herein may further comprise a purification step in order to obtain high purity extract. The purification step may include using activated carbon for decolourization.

The extracts of the present disclosure may be purified by repeating the extraction step(s) and the purification step(s) to obtain a high purity extract.

The present disclosure provides a pharmaceutical composition comprising at least p-coumaryl diacetate and ovatodiolide as active ingredients.

Ovatodiolide has a molecular formula $C_{20}H_{24}O_4$, named as 3,7,11,15(17)-cembratetraene-16,2:19,6-diolide-3484-37-5 (3E,12E)-3,12-dimethyl-8-methylene-6,18-dioxa-tricyclo [14.2.1.0.5,9]nonadeca-3,12,16(19)-triene-7,17-dione, and has the following chemical formula (2):

(2)

Ovatodiolide may be chemically synthesized or extracted from the plants, such as the plant *Anisomeles indica*. Taking the plant *Anisomeles indica* as an example, the root, stem, leaves, flowers or the whole plant of the plant *Anisomeles indica* may be extracted with the organic solvent(s). The polar solvents used in the present disclosure include C1-C12 alcohols, C2-C5 acetate esters, C5-C6 alkanes or the combinations thereof, and the exemplary solvents include methanol, ethanol, n-propanol, isopropanol, n-butanol, 2-butanol, 3-butanol, 1,3-butanediol, 1,4-butanediol, n-pentanol, isopentanol, 2,3-pentanediol, 2,4-pentanediol, cyclopentanol, hexanol, cyclohexanol, heptanol, octanol, nonanol, decanol, undecanol, dodecanol, ethyl acetate, propyl acetate, amyl acetate, n-pentane, cyclopentane, n-hexyl dioxane, cyclohexane or the combinations of thereof, but the solvents are not limited thereto. In one embodiment of the present disclosure, ethanol is used as the extraction solvent and the concentration of ethanol may be 50% to 95%, or 75% to 95% (v/v), for example.

The extraction temperature and time may be determined based on the nature of the solvent and other reaction conditions, and there are no particular limitations. In one embodiment of the present disclosure, the extraction temperature may be 50° C.~80° C., or 70° C.~80° C., and the extraction time may range from 2 hours to 4 hours.

The extraction method used herein may further comprise a purification step in order to obtain high purity extract. The purification step may include performing the purification through the column chromatography, thin-layer chromatography (TLC), high performance liquid chromatography (HPLC), gas chromatography or ion exchange. For example, the column chromatography with silica packed column(s) may be used for purification.

The extracts of the present disclosure may be purified by repeating the extraction step(s) and the purification step(s) to obtain a high purity extract.

The pharmaceutical composition of the present disclosure may further comprise one or more pharmaceutically acceptable auxiliaries, and the pharmaceutically acceptable auxiliaries may be non-toxic solid, semi-solid or liquid fillers, diluents, encapsulating materials, formulation adjuvants, or any conventional additives, excipients, preservatives, flavouring agents and the like. The pharmaceutically acceptable auxiliary, in the dosage and concentration used, is substantially non-toxic for the user, and should be compatible with other ingredients in the formulations. Specifically, for example, starch, corn starch, lactose, dextrin, cyclodextrin, methyl cellulose, carboxymethyl cellulose, sodium carboxymethyl cellulose, gelatin, gum, agar, guar gum, pectin, gum arabic, tragacanth, carrageenan or similar additives.

The pharmaceutical composition of the present disclosure may be administrated in any pharmaceutically acceptable form, and may be designed in appropriate dosage form in accordance with the route of the administration, for example, lozenges, capsules, film-coated tablets, powders, granules, syrups, suspensions, suppositories or patches. The route of the administration may include, for example, oral administration, rectal administration, nasal administration, topical administration, transdermal administration and the like. The pharmaceutical composition of the present disclosure can be prepared in the form of the topical compositions, such as an aqueous solution, aqueous gel, water-in-water, oil, water-in-oil or oil-in-water emulsion or cream, ointment or a paste. The active ingredients of the composition(s) of the present disclosure may be administrated in the form of pharmaceutically acceptable salts, or combined with other chemicals or drugs having the activity for relieving the symptoms of gout, in compatible ways to be administered in combination.

The pharmaceutical composition of the present disclosure includes at least an effective amount of one or more active ingredients, and the dosage or the ratio of each of the active ingredients of the present disclosure is not limited by the following embodiments. The pharmaceutical composition of the present disclosure may include one or more pharmaceutically acceptable auxiliaries. The term "effective amount" or "effective dosage" refers the amount of a compound or a substance that is enough to generate a desired effect toward the syndrome or disease for the patient receiving treatment. The exact amount or dosage may vary along with the purposes of treatment, and may be adjusted or determined based on those conventional techniques known in this field. For example, according to the weight, age, symptoms, affected locations or physiological conditions of the patient and/or the route of administration and other conditions, the physicians can choose the appropriate dosage and formulation.

In one embodiment of the present disclosure, the pharmaceutical composition at least comprises p-coumaryl diacetate and ovatodiolide as active ingredients, and the range of the weight ratio of p-coumaryl diacetate to ovatodiolide may be from 10:90 to 85:15, from 15:85 to 80:20, or preferably from 20:80 to 65:35. In another embodiment, the weight ratio of p-coumaryl diacetate and ovatodiolide is 50:50.

The literature articles cited herein are incorporated herein by reference. The following detailed descriptions of the present disclosure as well as the following examples are merely used to further explain the technical features of the present disclosure, not intended to limit the scope of the present invention.

Example 1

Preparation of p-Coumaryl Diacetate (Named as AG04-RA1 in the Following Examples)

Figure 1:
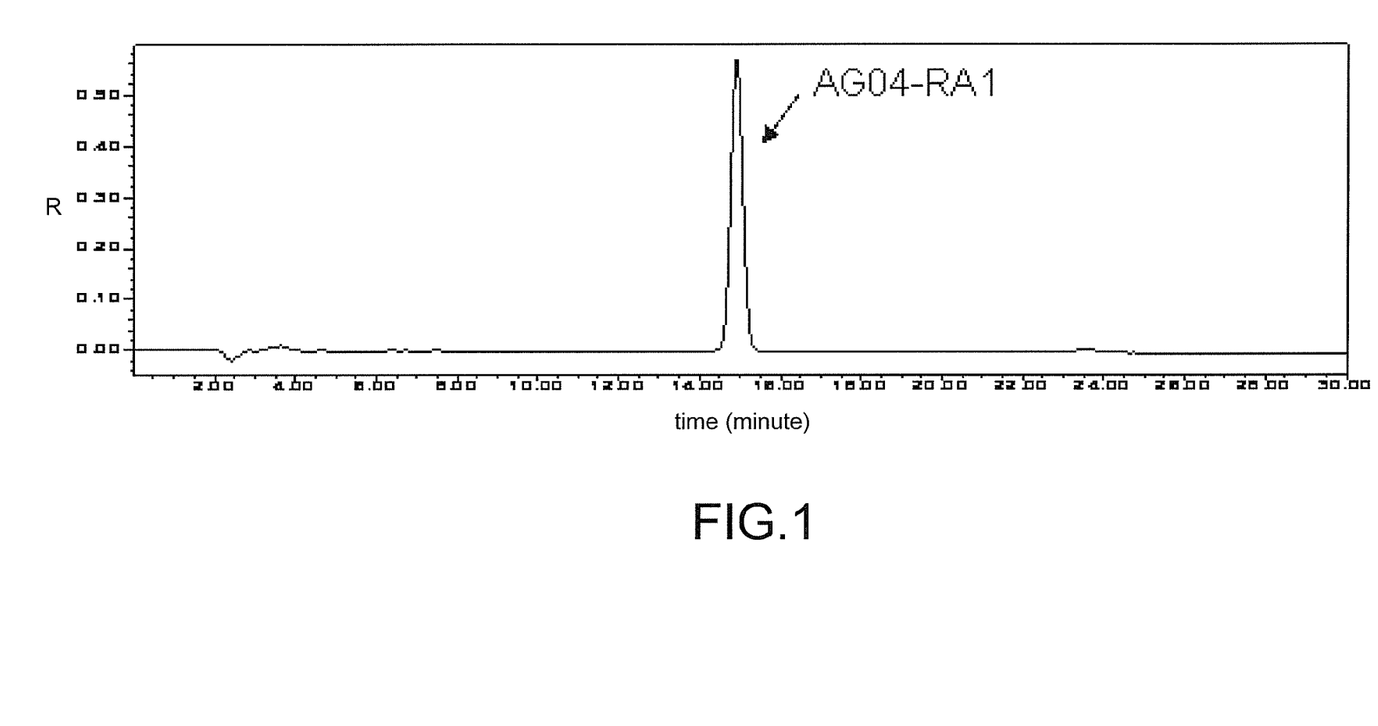
FIG. 1 is a HPLC chromatogram showing p-coumaryl diacetate prepared according to one embodiment of the present disclosure.

4 kilograms of the roots of the plant *Alpinia galanga* are grated, added with 30 liters of heptane and stirred for 72 hours at the room temperature, and filtered to separate the filtrate from the dregs. Then, the filtrate is added with active carbon for purification and decolourization, followed by distillation to remove heptane from the filtrate, so that 57.56 g of a pale yellow liquid is obtained. The obtained product is analyzed by high performance liquid chromatography using the reverse phase C18 chromatographic column gradient eluted with a mobile phase of 49% acetonitrile and with 51% of 0.05% trifluoroacetic acid aqueous solution. FIG. 1 is a HPLC chromatogram showing p-coumaryl diacetate according to the preparation as described in this embodiment. As shown in FIG. 1, the content and purity of p-coumaryl diacetate is shown in the chromatogram and the purity of the obtained p-coumaryl diacetate is about 80% to 95%. Further recrystallization of the obtained compound leads to white crystals having the purity of 99% (defined as "high purity" in this embodiment).

Example 2

Preparation of Ovatodiolide (Named as AG02-RA1 in the Following Examples)

Figure 2:
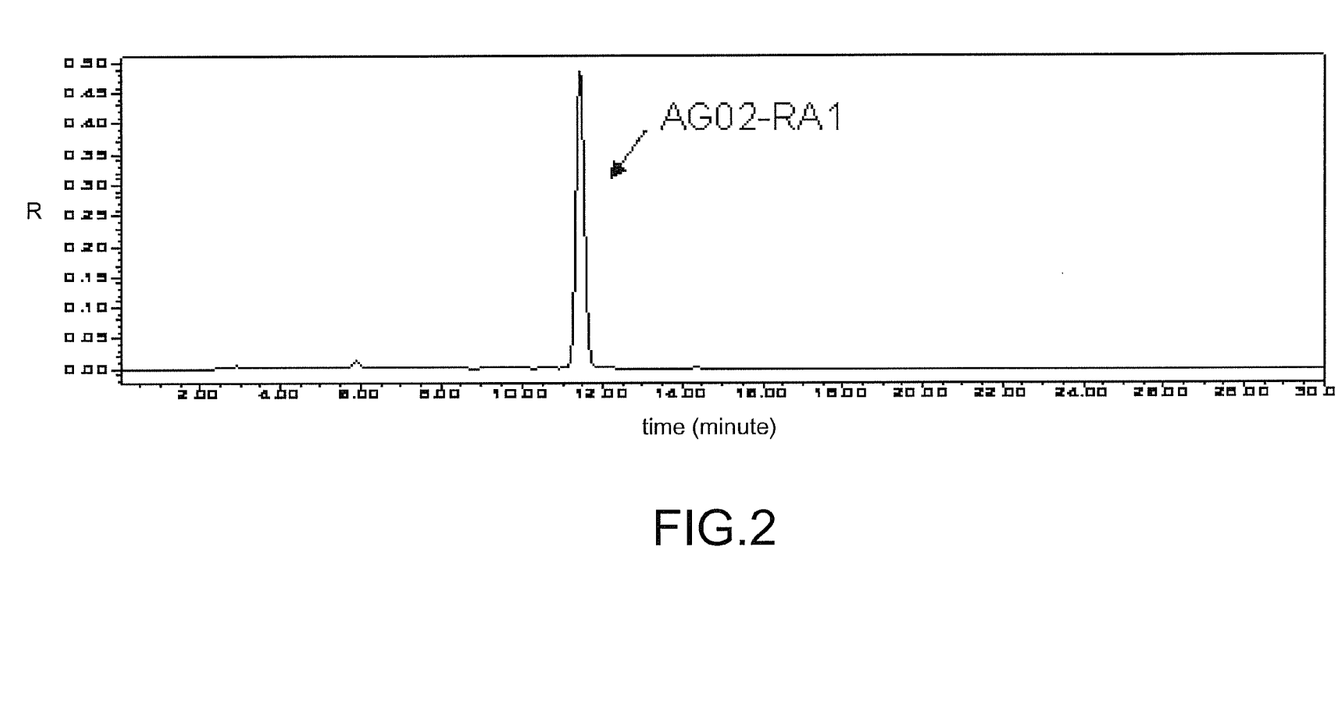
FIG. 2 is a HPLC chromatogram showing ovatodiolide prepared according to one embodiment of the present disclosure.

1 kg of the whole grass plant of the plant *Anisomeles indica* is chopped and extracted with 80% ethanol. The extracted liquid (extractant) is further concentrated to dryness, and then 1~3 times the volume of methanol is added. The insoluble solid is separated by filtration, and the filtrate is diluted with 3 volumes of water and then extracted with a solution of ethyl acetate and n-heptane at least one third of the total volume for 3 times. The organic layer of the extractant was concentrated to dryness to obtain the crude extract containing 40%~60% (w/w) of AG02. The crude extract is further dissolved in methanol in an amount of 6~12 times the weight of the solid and further decolorized with 1%~3% active carbon. Finally, the methanol solution is concentrated to dryness to obtain a mixture containing 70%~90% (w/w) of AG02-RA1. Further recrystallization of the obtained compound leads to white crystals having the purity of 98.1% (defined as "high purity" in this embodiment). The obtained product is analyzed by high performance liquid chromatography using the reverse phase C18 chromatographic column gradient eluted with a mobile phase of 49% acetonitrile and with 51% of 0.05% trifluoroacetic acid aqueous solution. FIG. 2 is a HPLC chromatogram showing ovatodiolide according to the preparation as described in this embodiment.

Example 3

Preparation of the Composition(s) Including p-Coumaryl Diacetate and Ovatodiolide The compound AG02-RA1 (2.5%~5%) prepared in Example 2 and the compound AG04-RA1 (1%~5%) prepared in Example 1 are dissolved in ethanol (final ethanol concentration being 10% (w/w)), then mixed with polyethylene glycol mixture solution (the mixture solution prepared by mixing poly ethylene glycol (MW 4000) and poly ethylene glycol (MW 400) and heated to 40° C.~80° C.), and cooled to the room temperature with stirring, so as to obtain the composition(s). The compositions can be prepared with different proportions of these two compounds and the compounds of different purities. Table 1 shows the ratios and purities of the compounds AG02-RA1 and AG04-RA1 in different compositions. In addition to the composition No. 7 using recrystallized high purity AG02-RA1 (purity: 98.1%) and AG04-RA1 (purity: 99%), the other compositions are prepared using the compounds AG02-RA1 of Example 2 and AG04-RA1 of Example 1. The composition No. 8 is used as the control (blank) and the composition No. 8 contains only the paste matrix material.

TABLE 1

| NO. | COMPOUND(S) | RATIO | PURITY |
|---|---|---|---|
| 1 | AG02-RA1 | paste matrix composition/AG02-RA1 (5%) | AG02-RA1: 87.72% |
| 2 | AG04-RA1 | paste matrix composition/AG04-RA1 (5%) | AG04-RA1: 79.98% |
| 3 | AG02-RA1: AG04-RA1 (50:50) | paste matrix composition/AG02-RA1 (2.5%)/AG04-RA1 (2.5%) | AG02-RA1: 87.72% AG04-RA1: 79.98% |
| 4 | AG02-RA1: AG04-RA1 (80:20) | paste matrix composition/AG02-RA1 (4%)/AG04-RA1 (1%) | AG02-RA1: 87.72% AG04-RA1: 79.98% |
| 5 | AG02-RA1 : AG04-RA1 (75:25) | paste matrix composition/AG02-RA1 (3.75%)/AG04-RA1 (1.25%) | |
| 6 | AG02-RA1: AG04-RA1 (50:50) | paste matrix composition/AG02-RA1 (2.5%)/AG04-RA1 (2.5%) | |
| 7 | AG02-RA1 : AG04-RA1 (50:50) (high purity) | paste matrix composition/AG02-RA1 (2.5%)/AG04-RA1 (2.5%) | AG02-RA1: 98.1% AG04-RA1: 99.0% |
| 8 | Control (blank) | paste matrix composition | |

Example 4

Animal Model to Assess the Activity of the Composition Including p-Coumaryl Diacetate and Ovatodiolide Mouse Air pouch model: this mouse model may be referenced to the methods and the experimental details as in the published article "Role of S100A8 and S100A9 in neutrophil recruitment in response to monosodium urate monohydrate crystals in the air-pouch model of acute gouty arthritis", *Arthritis Rheum* 2003 August, 48(8):2310-20. The full content of such document as a whole is incorporated by reference herein and made a part of this specification.

Before the experiment, the mice are shaved to remove back hair. At day 0 sterile filtered air (2 ml/per mouse) is injected through 0.22 μm microfilter to the back of each mouse subcutaneously, so that a pseudosynovial cavity is formed in each mouse. At day 3, an air booster (3 ml/mouse) is again given to each mouse, so that the air pouch is maintained round. Later, the mice are weighed and grouped so that the average weight of the mice in each group is about the same. At day 6 monosodium urate (MSU) crystal suspension (5 mg in 2 ml/per mouse) is injected into the air pouch. Topical application of the paste (100 mg paste/per mouse) is administrated 15 hours prior to MSU stimulation. At a specific time (5 hours) after the injection of MSU, the mice were euthanized with an excess of carbon dioxide, 2 ml PBS per mouse is injected into the air pouch, and the air pouch is carefully cut to collect the exudate. The collected exudate is subjected to the centrifugation at 1,000 rpm, 4° C. for 5 minutes, and the supernatant is then placed in a 96-well plate and stored at −20° C. An ELISA kit (purchased from R&D Systems) is used to analyze the contents of IL-1β and IL-6 in the exudate. The precipitate is resuspended and reacted with 1 ml red blood cell lysis buffer (RBC lysis buffer) for one minute to remove the red blood cells, followed by adding 1 ml PBS to terminate the reaction, centrifuged at 1,000 rpm, 25° C. for 5 minutes, and the supernatant is discarded. The precipitate is then resuspended in 1 ml PBS as the cell suspension and the cell suspension is filtered by filter membrane (BD Falcon 100 μm Nylon filter strainer) and the filtered cell suspension is dispensed into several tubes (0.25 ml/tube) for subsequent cell counting or for labelling with various differentiation antigen markers (such as cluster of differentiation (CD) markers). The flow cytometry is used for cell counting of the various cells.

In order to investigate the anti-gout efficacy of AG02-RA1 and AG04-RA1, either used alone or in combination, the experiments are performed to test AG02-RA1 alone, AG04-RA1 alone and the combination (s) of AG02-RA1:AG04-RA1 in the ratio of 50:50 (Composition Nos. 1, 2 and 3 as shown in Table 1). The total weight of the content of AG02-RA1 and/or AG04-RA1 is 5 mg, accounting for 5 wt % of the total weight of the test sample paste composition. For example, the total weight of the test sample paste composition is 100 mg, the composition of the sample No. 1 (Composition No. 1) contains 5 mg of AG02-RA1, the sample No. 2 contains 5 mg of AG04-RA1, and the sample No. 3 contains 2.5 mg of AG02-RA1 and 2.5 mg of AG04-RA1.

The experimental results are shown in the following Table and paragraphs, and in Table 2, leukocyte surface antigen makers are used to show the results of measured leukocyte cell (CD45$^+$ cells) density, under the administration of AG02-RA1 and/or AG04-RA1, either alone or in combination. The results indicate that the administration of the combination of AG02-RA1 and AG04-RA1, each individually 2.5 mg, leads to the best result in the suppression of the number (amount) of leukocytes.

TABLE 2

| NO. | COMPOUND(S) | AVERAGE VALUES | T-TEST | INHIBITION RATE | TEST NO. |
|---|---|---|---|---|---|
| 1 | 0 mg AG02-RA1+ AG04-RA1 (No AG02-RA1 and AG04-RA1/ blank control) | 803 | — | — | 5 |
| 2 | 5 mg AG02-RA1 | 1609 | 0.099 | −100% | 5 |
| 3 | 5 mg AG04-RA1 | 670 | 0.720 | 17% | 5 |
| 4 | 2.5 mg AG02-RA1 + 2.5 mg AG04-RA1 | 489 | 0.315 | 39% | 5 |

* The average values are the average values of the normalized leukocyte cell density (unit: cells*10$^3$/ml) obtained by cell counting analysis.

The experimental results are shown in the following Table and paragraphs, and in Table 3, neutrophil surface antigen makers are used to show the results of measured neutrophil cell (CD45$^+$/Ly6G$^+$ cells) density, under the administration of AG02-RA1 and/or AG04-RA1, either alone or in combination. The results indicate that the sole administration of 5 mg of AG02-RA1 leads to the best result in the suppression of the number of neutrophils. In addition, the sole administration of 5 mg of AG04-RA1 is effective for suppressing the amount of the neutrophils.

TABLE 3

| NO. | COMPOUND(S) | AVERAGE VALUES | T-TEST | INHIBITION RATE | TEST NO. |
|---|---|---|---|---|---|
| 1 | 0 mg AG02-RA1 + AG04-RA1 (blank control) | 360 | — | — | 5 |
| 2 | 5 mg AG02-RA1 | 133 | 0.204 | 63% | 5 |
| 3 | 5 mg AG04-RA1 | 205 | 0.366 | 43% | 5 |
| 4 | 2.5 mg AG02-RA1 + 2.5 mg AG04-RA1 | 255 | 0.536 | 21% | 5 |

* The average values are the average values of the normalized leukocyte cell density (unit: cells*10$^3$/ml) obtained by cell counting analysis.

Figure 3:
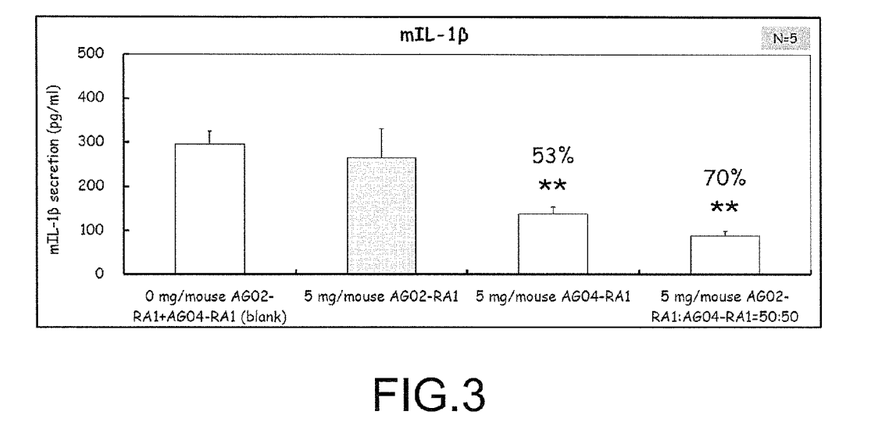
FIG. 3 shows the secretion amount of interleukin-1β as stripes following the administration of the test samples according to one embodiment of the present disclosure.
Figure 4:
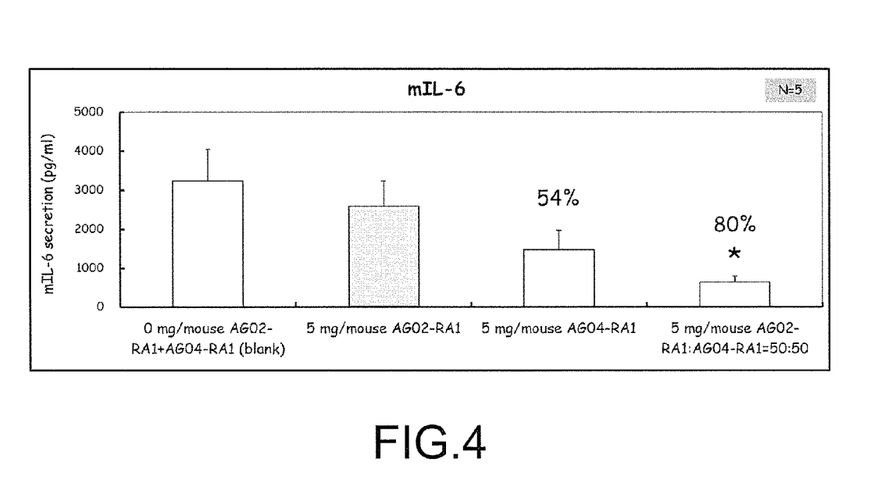
FIG. 4 shows the secretion amount of interleukin-6 as stripes following the administration of the test samples according to one embodiment of the present disclosure.

FIGS. 3 and 4 show the secretion amounts of interleukin-1β (mIL-1β) and interleukin-6 (mIL-6) as stripes after the application of different test samples, so as to explore the anti-gout efficacy thereof. The percentages (%) shown in FIGS. 3-4 represent the inhibition rates in percentages, while the asterisk"*" shown in the figures represents that when the group compared with the control blank group, there were significant differences (P<0.05). It is known that interleukin-1β is significantly associated with the level of the pain, and can be used as one of the major indicators for monitoring the main symptoms of gout. The experimental results show that either for the suppression of interleukin-1β or interleukin-6, the administration of the combination of each 2.5 mg of AG02-RA1 and AG04-RA1 is most effective in the suppression of the amount of interleukin-1β and interleukin-6 with the inhibition rate of 70% and 80% respectively. Also, the sole administration of 5 mg AG04-RA1 shows good inhibitory effect (the inhibition rate >50%).

Example 5

Animal Model to Assess the Activity of the Compositions Including p-Coumaryl Diacetate and Ovatodiolide in Different Proportions The animal model as described in Example 4 will not be repeated herein. The combinations of the test samples investigated in Example 4 are applied to evaluate the activity of the test samples, and the following results are shown. From the previous examples, the combinational usage of AG02-RA1 and AG04-RA1 shows better results than the application of one single ingredient. Then, different proportions of AG02-RA1 and AG04-RA1 used in combination (as shown in Table 1, sample Nos. 4, 5 and 6) to investigate the anti-gout effect in the following experiments, and to find the suitable ratios (proportions) and the effective range for the compatibility of ingredients in the formulation. The ratios of AG02-RA1: AG04-RA1 to be tested may be 80:20, 75:25 or 50:50. For example, the overall weight of each test sample is 100 mg, the sample No. 4 contains 4 mg of AG02-RA1 and 1 mg of AG04-RA1, a total weight of 5 mg of AG02-RA1 and AG04-RA1, accounting for 5% of the total weight of the test sample. The weight ratios or percentages of the other test samples can be determined accordingly.

The experimental results are shown in Table 4, and leukocyte surface antigen makers are used to show the results of measured leukocyte cell (CD45+ cells) density, under the administration of different proportions of AG02-RA1 and AG04-RA1. The results indicate that the administration of the combination of AG02-RA1 and AG04-RA1, either in the ratio of AG02-RA1:AG04-RA1 of 80:20 or 75:25, leads to the satisfactory suppression of the number (amount) of leukocytes. The ratio of AG02-RA1:AG04-RA1 of 80:20 or 75:25 is within the valid range for suppressing the amount of leukocytes.

TABLE 4

| NO. | COMPOUND(S) | AVERAGE VALUES | T-TEST | INHIBITION RATE | TEST NO. |
|---|---|---|---|---|---|
| 1 | 0 mg AG02-RA1 + AG04-RA1 (No AG02-RA1 and AG04-RA1/ blank control) | 625 | — | — | 5 |
| 2 | AG02-RA1: AG04-RA1 (80:20) | 345 | 0.22 | 45% | 5 |
| 3 | AG02-RA1: AG04-RA1 (75:25) | 196 | 0.07 | 69% | 5 |
| 4 | AG02-RA1: AG04-RA1 (50:50) | 113 | 0.04 | 82% | 5 |

* The average values are the average values of the normalized leukocyte cell density (unit: cells*10³/ml) obtained by cell counting analysis.

The experimental results are shown in Table 5, and neutrophil surface antigen makers are used to show the results of measured neutrophil cell (CD45+/Ly6G+ cells) density, the administration of different proportions of AG02-RA1 and AG04-RA1. The results indicate that the administration of the combination of AG02-RA1 and AG04-RA1, either in the ratio of AG02-RA1:AG04-RA1 of 80:20 or 75:25, leads to the satisfactory suppression of the number of neutrophils. The ratio of AG02-RA1:AG04-RA1 of 80:20 or 75:25 is within the valid range for suppressing the amount of the neutrophils.

TABLE 5

| NO. | COMPOUND(S) | AVERAGE VALUES | T-TEST | INHIBITION RATE | TEST NO. |
|---|---|---|---|---|---|
| 1 | 0 mg AG02-RA1 + AG04-RA1 (No AG02-RA1 and AG04-RA1/ blank control) | 285 | — | — | 5 |
| 2 | AG02-RA1: AG04-RA1 (80:20) | 153 | 0.28 | 46% | 5 |
| 3 | AG02-RA1: AG04-RA1 (75:25) | 128 | 0.22 | 55% | 5 |
| 4 | AG02-RA1: AG04-RA1 (50:50) | 29 | 0.06 | 90% | 5 |

* The average values are the average values of the normalized leukocyte cell density (unit: cells*10³/ml) obtained by cell counting analysis.

Figure 5:
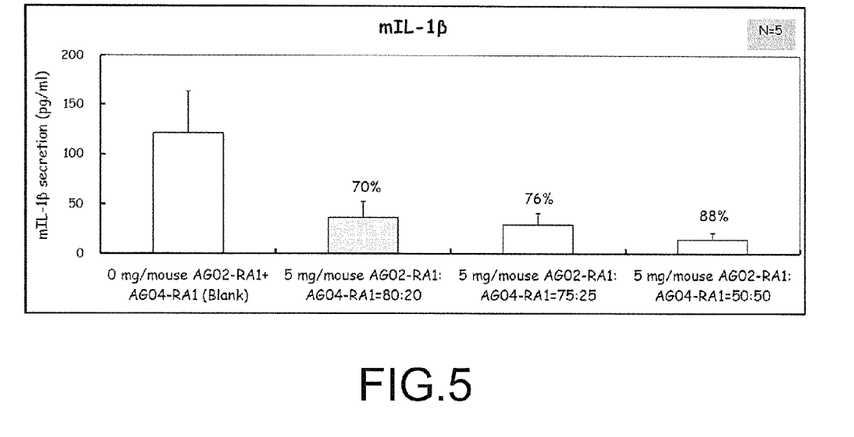
FIG. 5 shows the secretion amount of interleukin-1β as stripes following the administration of the test samples according to another embodiment of the present disclosure.
Figure 6:
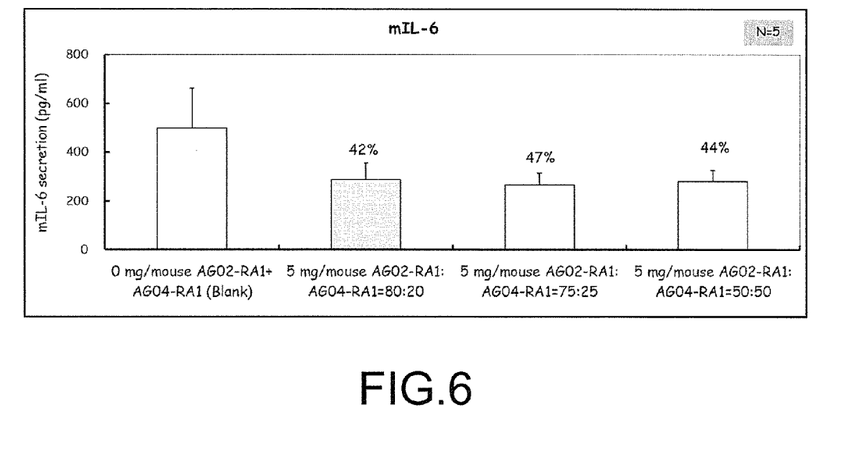
FIG. 6 shows the secretion amount of interleukin-6 as stripes following the administration of the test samples according to another embodiment of the present disclosure.

FIGS. 5 and 6 show the secretion amounts of interleukin-1β (mIL-1β) and interleukin-6 (mIL-6) as stripes after the application of different test samples, so as to explore the anti-gout efficacy thereof. The percentages (%) shown in FIGS. 5-6 represent the inhibition rates in percentages. The experimental results show that either for the suppression of interleukin-1β or interleukin-6, the administration of the combination of AG02-RA1 and AG04-RA1, either in the ratio of AG02-RA1:AG04-RA1 of 80:20 or 75:25, leads to the satisfactory suppression of interleukin-1β and interleukin-6. The ratio of AG02-RA1:AG04-RA1 of 80:20 or 75:25 is within the valid range for the suppression of interleukin-1β or interleukin-6.

Example 6

Animal Model to Assess the Activity of the Compositions Including p-Coumaryl Diacetate and Ovatodiolide of Different Purities The animal model as described in Example 4 will not be repeated herein. From the previous examples, the combinational usage of AG02-RA1 and AG04-RA1 shows good results. Then, AG02-RA1 and AG04-RA1 of the ordinary purity or high purity are used in combination (as shown in Table 1, sample Nos. 6 and 7) to investigate the anti-gout effect in the following experiment. The ratio of AG02-RA1: AG04-RA1 to be tested is 50:50.

The experimental results are shown in Table 6, and leukocyte surface antigen makers are used to show the results of measured leukocyte cell (CD45+ cells) density, under the administration of the combination of AG02-RA1 and AG04-RA1 of different purities. The results indicate that AG02-RA1 and AG04-RA1 of the higher purity achieves more effective suppression of the number of leukocytes.

TABLE 6

| NO. | COMPOUND(S) | AVERAGE VALUES | T-TEST | INHIBITION RATE | TEST NO. |
|---|---|---|---|---|---|
| 1 | 0 mg AG02-RA1 + AG04-RA1 (No AG02-RA1 and AG04-RA1/ blank control) | 311 | — | — | 5 |
| 2 | AG02-RA1: AG04-RA1 (50:50) | 130 | 0.14 | 58% | 5 |
| 3 | AG02-RA1: AG04-RA1 (50:50)(high purity) | 61 | 0.06 | 80% | 5 |

* The average values are the average values of the normalized leukocyte cell density (unit: cells*10³/ml) obtained by cell counting analysis.

The experimental results are shown in Table 7, and neutrophil surface antigen makers are used to show the results of measured neutrophil cell (CD45+/Ly6G+ cells) density, the administration of AG02-RA1 and AG04-RA1 of different purities. The results indicate that AG02-RA1 and AG04-RA1 of the higher purity (50:50 high purity) achieves more effective suppression of the number of neutrophils.

TABLE 7

| NO. | COMPOUND(S) | AVERAGE VALUES | T-TEST | INHIBITION RATE | TEST NO. |
|---|---|---|---|---|---|
| 1 | 0 mg AG02-RA1 + AG04-RA1 (No AG02-RA1 and AG04-RA1/ blank control) | 256 | — | — | 5 |

TABLE 7-continued

| NO. | COMPOUND(S) | AVERAGE VALUES | T-TEST | INHIBITION RATE | TEST NO. |
|---|---|---|---|---|---|
| 2 | AG02-RA1: AG04-RA1 (50:50) | 84 | 0.10 | 67% | 5 |
| 3 | AG02-RA1: AG04-RA1 (50:50) (high purity) | 24 | 0.04 | 91% | 5 |

* The average values are the average values of the normalized leukocyte cell density (unit: cells*10³/ml) obtained by cell counting analysis.

Figure 7:
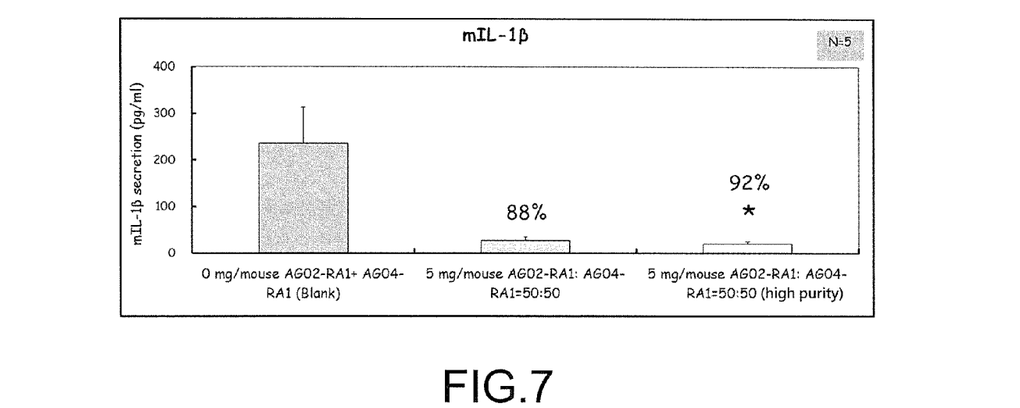
FIG. 7 shows the secretion amount of interleukin-1β as stripes following the administration of the test samples according to one embodiment of the present disclosure.
Figure 8:
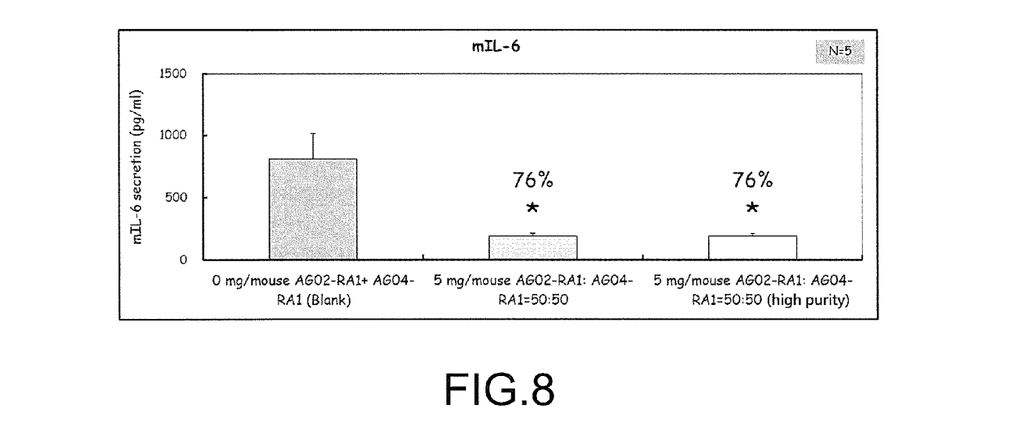
FIG. 8 shows the secretion amount of interleukin-6 as stripes following the administration of the test samples according to one embodiment of the present disclosure.

FIGS. 7 and 8 show the secretion amounts of interleukin-1β (mIL-1β) and interleukin-6 (mIL-6) as stripes after the application of different test samples, so as to explore the anti-gout efficacy thereof. The percentages (%) shown in FIGS. 7-8 represent the inhibition rates in percentages, while the asterisk "*" shown in the figures represents that when the group compared with the control blank group, there were significant differences (P<0.05). The experimental results show that either for the suppression of interleukin-1β or interleukin-6, the administration of the combination of AG02-RA1 and AG04-RA1 of the higher purity (50:50 high purity) shows better inhibitory effect.

It is concluded that the composition of the present disclosure containing p-coumaryl diacetate is effective for the alleviation or treatment of gout, and when the composition of the present disclosure further includes ovatodiolide, the anti-gout effect becomes more significant. The composition(s) of the present disclosure is potential and may be developed as an anti-gout drug.

The compositions of the present disclosure are not limited to the dosage or proportions as described in the previous embodiments and may be liberally mixed or used in combination with any other pharmaceutical acceptable auxiliaries or other therapeutic agents.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A pharmaceutical composition, comprising p-coumaryl diacetate and ovatodiolide in a weight ratio of p-coumaryl diacetate to ovatodiolide ranging from 10:90 to 85:15.

2. The composition as recited in claim 1, wherein the weight ratio of p-coumaryl diacetate to ovatodiolide is 50:50.

3. The composition as recited in claim 1, wherein p-coumaryl diacetate is chemically synthesized or extracted from a plant.

4. The composition as recited in claim 3, wherein p-coumaryl diacetate is extracted from the plant *Alpinia galanga*.

5. The composition as recited in claim 1, wherein ovatodiolide is chemically synthesized or extracted from a plant.

6. The composition as recited in claim 5, wherein ovatodiolide is extracted from the plant *Anisomeles indica*.

7. A method for alleviating or treating gout by administrating a medicament comprising a pharmaceutical composition that comprises p-coumaryl diacetate as an active ingredient.

8. The method as recited in claim 7, wherein the pharmaceutical composition further comprises ovatodiolide.

9. The method as recited in claim 8, wherein a weight ratio of p-coumaryl diacetate to ovatodiolide in the pharmaceutical composition ranging from 10:90 to 85:15.

10. The method as recited in claim 9, wherein the weight ratio of p-coumaryl diacetate to ovatodiolide is 50:50.

11. The method as recited in claim 7, wherein p-coumaryl diacetate is chemically synthesized or extracted from a plant.

12. The method as recited in claim 11, wherein p-coumaryl diacetate is extracted from the plant *Alpinia galanga*.

13. The method as recited in claim 8, wherein ovatodiolide is chemically synthesized or extracted from a plant.

14. The method as recited in claim 13, wherein ovatodiolide is extracted from the plant *Anisomeles indica*.

* * * * *